US012596085B2

(12) United States Patent (10) Patent No.: US 12,596,085 B2

Tu (45) Date of Patent: Apr. 7, 2026

(54) METHOD AND APPARATUS FOR SIMULTANEOUSLY MEASURING AIR CONTAINED HYDROGEN AND WATER VAPOR CONCENTRATIONS VIA A SINGLE MEMS THERMAL CONDUCTIVITY SENSOR

(71) Applicant: Posifa Technologies Inc., San Jose, CA (US)

(72) Inventor: Peng Tu, Palo Alto, CA (US)

( * ) Notice: Subject to any disclaimer, the term of this patent is extended or adjusted under 35 U.S.C. 154(b) by 301 days.

(21) Appl. No.: 18/222,481

(22) Filed: Jul. 17, 2023

(65) Prior Publication Data

US 2025/0027893 A1 Jan. 23, 2025

(51) Int. Cl.
G01N 25/18 (2006.01)
G01N 33/00 (2006.01)

(52) U.S. Cl.
CPC ......... G01N 25/18 (2013.01); G01N 33/0062 (2013.01); G01N 33/0073 (2013.01); *G01N 33/0068* (2024.05)

(58) Field of Classification Search
CPC ............... G01N 25/18; G01N 33/0062; G01N 33/0073; G01N 33/0068
See application file for complete search history.

(56) References Cited

U.S. PATENT DOCUMENTS

2020/0333273 A1* 10/2020 Hedrich ................ G01F 1/6888
2021/0123876 A1* 4/2021 Carr ........................ G01N 27/18

FOREIGN PATENT DOCUMENTS

WO WO-2020080003 A1 * 4/2020 ............. G01N 27/18

* cited by examiner

*Primary Examiner* — Benjamin R Schmitt
(74) *Attorney, Agent, or Firm* — JW Law Group; James M. Wu

(57) ABSTRACT

A single MEMS thermal conductivity sensor based system capable of simultaneously measuring an air containing hydrogen and water vapor concentrations is described. The hydrogen and water vapor have different temperature coefficients of thermal conductivities and the sensor calculates their concentrations by their contributions to the total thermal conductivity of the air containing hydrogen and water vapor at different modulation temperatures of the sensor. The sensor comprises a one-dimensional gas heat conduction chamber is used to measure the temperature difference between the heat source on the top and heat sink on the bottom of the chamber. The hydrogen and water vapor concentrations can be calculated using the measured thermal conductivities of the air contained hydrogen and water vapor at different modulation temperatures of the sensor.

40 Claims, 4 Drawing Sheets

METHOD AND APPARATUS FOR SIMULTANEOUSLY MEASURING AIR CONTAINED HYDROGEN AND WATER VAPOR CONCENTRATIONS VIA A SINGLE MEMS THERMAL CONDUCTIVITY SENSOR

FIELD OF THE INVENTION

The present invention relates generally to a single MEMS thermal conductivity sensor based system capable of simultaneously measuring the component concentrations of a gas mixture and more particularly to a single MEMS thermal conductivity sensor based system capable of simultaneously measuring air contained hydrogen and water vapor concentrations.

BACKGROUND

The use of hydrogen for industrial purposes has grown dramatically over the past few decades, and future projections indicate that its use will continue to grow on pace with demand for energy. Hydrogen consumption is dominated by petroleum refining, treating metals, producing fertilizer, and processing foods.

The use of hydrogen in the production of these fuels has more than tripled since 1975. This growth trend will likely continue, with future projections indicating that the global hydrogen market value will exceed $160 billion (US) by 2026. Growth will be fueled by the expansion of refining facilities across developing countries and more extensive use in metal and semiconductor applications. But the increased use of hydrogen also calls for greater abilities to detect hydrogen leaks quickly to prevent hazardous conditions.

Several hydrogen sensing and detection mechanisms have been studied early since 1900. The traditional mechanisms are still used widely in industry such as Gas Chromatography (GC), Mass Spectrometry (MS), Catalytic Bead (CB) and Thermal Conductivity (TC).

U.S. Pat. No. 11,333,625 B2 (Electrochemical hydrogen sensor) disclosed a hydrogen electrochemical sensor. An electrochemical sensor is typically contains two or three electrodes: the working electrode, reference electrode (three electrode sensors only) and counter electrode. These electrodes are stacked parallel to each other, separated by a thin layer of electrolyte. The working electrode is also in contact with the ambient air to be measured, normally via a gas diffusion layer. These sensors essentially operate on the same principle as fuel cells. Hydrogen is oxidized when it comes in contact with the working electrode. At the counter electrode, the other molecule, such as oxygen, is reduced. This results in generation of an electrical current between the two electrodes, proportional to the hydrogen concentration. The reference electrode has a stable potential from which no current is drawn. It is used to eliminate interference from side reactions with the counter electrode. The electrochemical sensors are stable with lifetimes of up to two years, which is significantly less than the DOE target of 10 years. Limitations include a restricted temperature range due to a liquid electrolyte, moderate selectivity (e.g., CO can affect the sensor), and a dependence on environmental pressure. Due to deterioration of the electrode catalyst the sensitivity of the sensors decreases with time.

WO2014189119A1 (Hydrogen gas sensor with concentration function and hydrogen gas sensor probe used in same) disclosed a hydrogen metal oxide semiconductor sensor. A metal oxide semiconductor sensor typically has three layers: a metal layer, an oxide layer and a semiconductor layer (similar to capacitors). The capacitance of these sensors varies with the applied voltage and the width of the depletion region affect the value of capacitance. In the presence of hydrogen, atoms are absorbed at the interface of the oxide, changing the work function of the metal layer of the sensor. The metal oxide semiconductor sensor is not considered as a selective device, a cross sensitivity problems, such as moisture variations which can also affect the calibration curve. The response of the sensor is not linear and a long response time and even longer recovery time is another disadvantage.

While other solid-state technologies such as semiconducting metal oxide and catalytic bead, need heating the catalysts to about 300° C. to sense hydrogen, which may be considered as an ignition source, so it is dangerous. In general, catalytic bead sensors are non-selective for hydrogen.

Most of traditional thermal conductivity sensors utilize thermistors whose resistance is strongly dependent on temperature. The sensor is not heated to a temperature that induces combustion, but only to a temperature where the resistance of the thermistors deviates from the linear limit of Ohm's law. A linear increase in current is observed as a low voltage is applied to the thermistors. In an I-V plot the slope of the linear region is the reciprocal resistance (1/R) of the thermistors. As the applied electrical power (I-V) increases, the ability to dissipate heat to the surrounding environment (air matrix) is exceeded, resulting in increasing the temperature of the thermistors. The resistance no longer remains constant and a deviation from a linear I-V plot is observed.

Since thermal transport between solid and gas dependents on the temperature, density, and composition of the gas, these sensors are affected by environmental parameters such as temperature, pressure and humidity. As with many technologies the environmental effects can be compensated, but this requires independent measurement for ambient conditions.

So it's clear that each hydrogen sensor has its advantages and disadvantages and there is no specific method that can be used for sensing the leakage of hydrogen in all applications and conditions.

SUMMARY OF THE INVENTION

The object of the invention is to solve or alleviate some or all of the problems described above. More specifically, it is an object of the present invention to provide a single MEMS thermal conductivity hydrogen sensor based system capable of simultaneously measuring an air contained hydrogen and water vapor concentrations which is operated based on: hydrogen and water vapor have different temperature coefficients of their thermal conductivities and the sensor can be modulated by temperature so as to calculate their concentrations by their contributions to the total thermal conductivity of the air contained hydrogen and water vapor at different modulation temperatures of the sensor.

It is another object of the present invention to provide a hydrogen sensor being highly selectively to hydrogen and having long term stability and consistent reproducibility.

It is still another object of the present invention to provide a hydrogen sensor indicating a hydrogen concentration in the range 0.01 to 10% or 1-100% (fuel cells).

It is still another object of the present invention to provide a hydrogen sensor operable in the range of temperature −30 to 80° C. (safety) and −70 to 150° C. (fuel cells).

It is still another object of the present invention to provide a hydrogen sensor operable the range of relative humidity (10 to 98%).

It is still another object of the present invention to provide a hydrogen sensor with fast response and recovery time (<20 ms).

It is still another object of the present invention to provide a hydrogen sensor with long life time (>5 years).

Other aspects and features of the present invention will become apparent to those ordinarily skilled in the art upon review of the following description of the invention in conjunction with the accompanying figures.

BRIEF DESCRIPTION OF THE DRAWINGS

The invention will now be described in more detail with reference to the accompanying, schematic drawings in the range of −40 to 100° C. at one atmosphere.

DETAILED DESCRIPTION

All gases conduct heat to differing degrees, and the amount of heat transferred by a gas is determined by its thermal conductivity value. This property can be exploited in sensing because each gas has a different thermal conductivity value.

Figure 1:
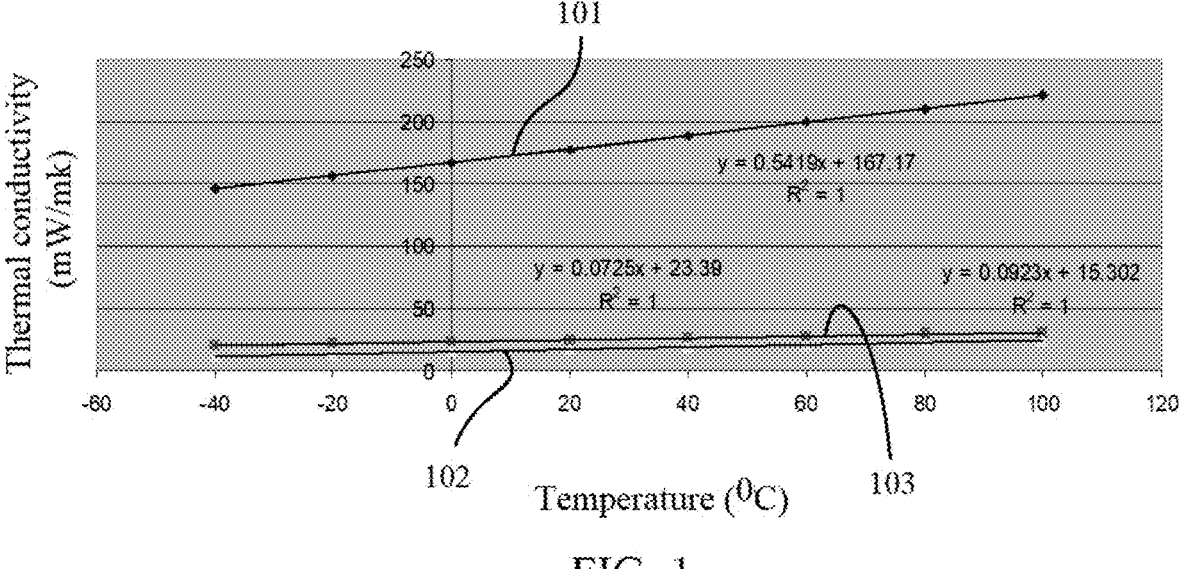
FIG. 1 is a diagram showing the thermal conductivities of air, hydrogen and water vapor as functions of temperature in the range of −40 to 100° C. at one atmosphere.

Reference to FIG. 1, which is a diagram showing the thermal conductivities of air, hydrogen and water vapor as functions of temperature in the range of −40 to 100° C. at one atmosphere. The thermal conductivity data is taken from the thermal conductivity of gases chart of Engineering Supplies and Book Store. In FIG. 1, 101 is the curve showing the thermal conductivity of hydrogen as a function of temperature in the range of −40 to 100° C. at one atmosphere. The curve has a slope 0.5419 and a $R^2$ value 1. 102 is the curve showing the thermal conductivity of air as a function of temperature in the range of −40 to 100° C. at one atmosphere. The curve has a slope 0.0725 and a $R^2$ value 1. 103 is the curve showing the thermal conductivity of water vapor as a function of temperature in the range of −40 to 100° C. at one atmosphere. The curve has a slope 0.0923 and a $R^2$ value 1.

A following formula has been used the definition of properties of multi-component fluid from the properties of the individual components:

$$\alpha = \sum Y_i \alpha_i \qquad (1)$$

Where $\alpha$ is an arbitrary constitutive fluid property, Yi is the molar fraction of component i, and i correspondingly is the component index.

Equation (1) is nothing else but mass averaging and is used for the definition of the laminar viscosity, the specific heat at constant volume, the specific heat at constant pressure, and the laminar thermal conductivity in multi-component mixtures. One can reasonably assume that the molar averaging:

$$k = \sum N_i k_i \qquad (2)$$

Where k is the thermal conductivity of an air contained hydrogen and water vapor and Ni is the molar fractions of air, hydrogen and water vapor.

Figure 2:
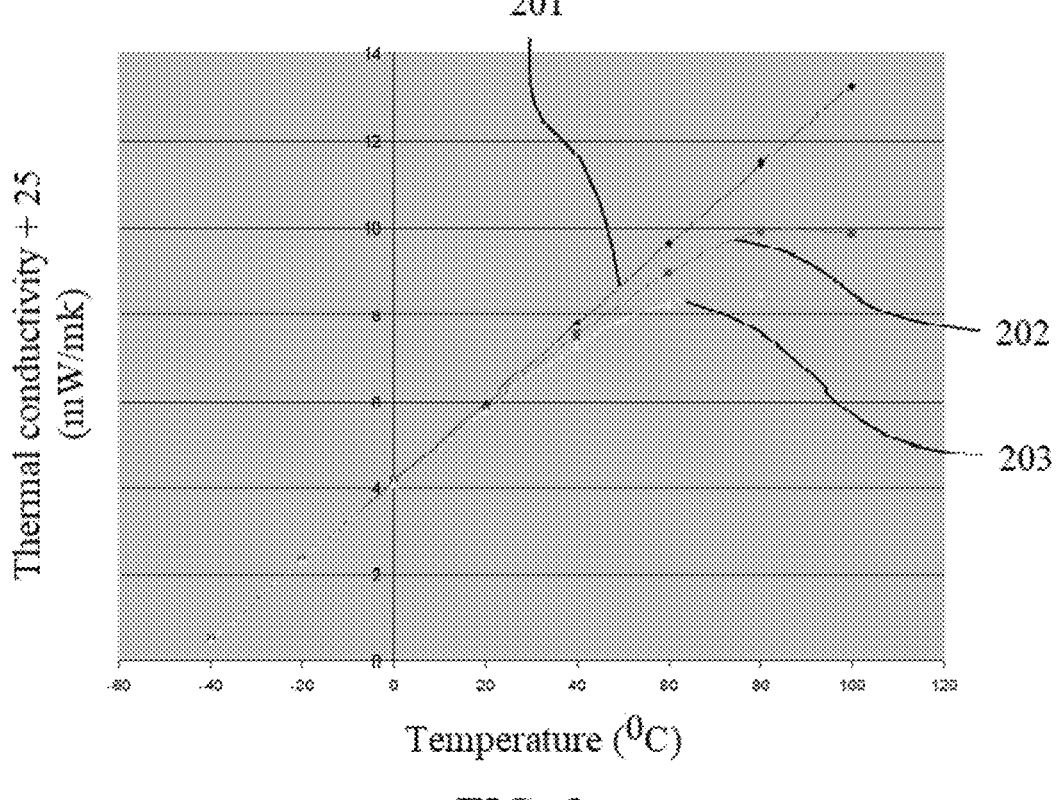
FIG. 2 is a diagram showing the thermal conductivities of a gas mixture of 4% hydrogen in air and 4% hydrogen in wet air as functions of temperature.

Reference to FIG. 2, which is a diagram showing the thermal conductivities of a mixture of 4% hydrogen in air and 4% hydrogen in wet air as functions of temperature in the range of −40 to 100° C. at one atmosphere. In FIG. 2, 201 is the curve of the thermal conductivity of 4% hydrogen in dry air as a function of temperature in the range of −40 to 100° C. at 1 atmosphere, 202 is the curve of the thermal conductivity of 4% hydrogen in a relative humidity (RH) 50% air as a function of temperature in the range of −40 to 100° C. at one atmosphere, 203 is the curve of the thermal conductivity of 4% hydrogen in a relative humidity (RH) 98% air as a function of temperature in the range of −40 to 100° C. at one atmosphere. In the above limited ranges compare with an experiment measurement data the mass averaging approximate is acceptable.

There is an urgent need to develop highly selective hydrogen sensors for environmental, residential, and industrial applications. Here, we propose a highly selective multiple gases detection system using a single MEMS thermal conductivity sensor.

The operation principle of the sensor is based on a special thermal conductivity and a special temperature coefficient of the thermal conductivity of each gas including air contained hydrogen and water vapor. The concentration of individual gas of a gas mixture does not change with temperature but the total thermal conductivity of the gas mixture does. So it is possible to calculate the concentrations of each gas by change the temperature so as to change the total thermal conductivity of the gas mixture and the individual thermal conductivity of each gas.

MEMS are a silicon chip-based fabrication technology, known as a Micro Electro-Mechanical System. MEMS technology has been grown significantly for different sorts of sensors. For thermal conductivity sensors the surface to volume ration of sensing material have been increased substantially, which has ultimately reduced not only the heating power but also the response time and recover time of the thermal conductivity sensors.

Figure 3:
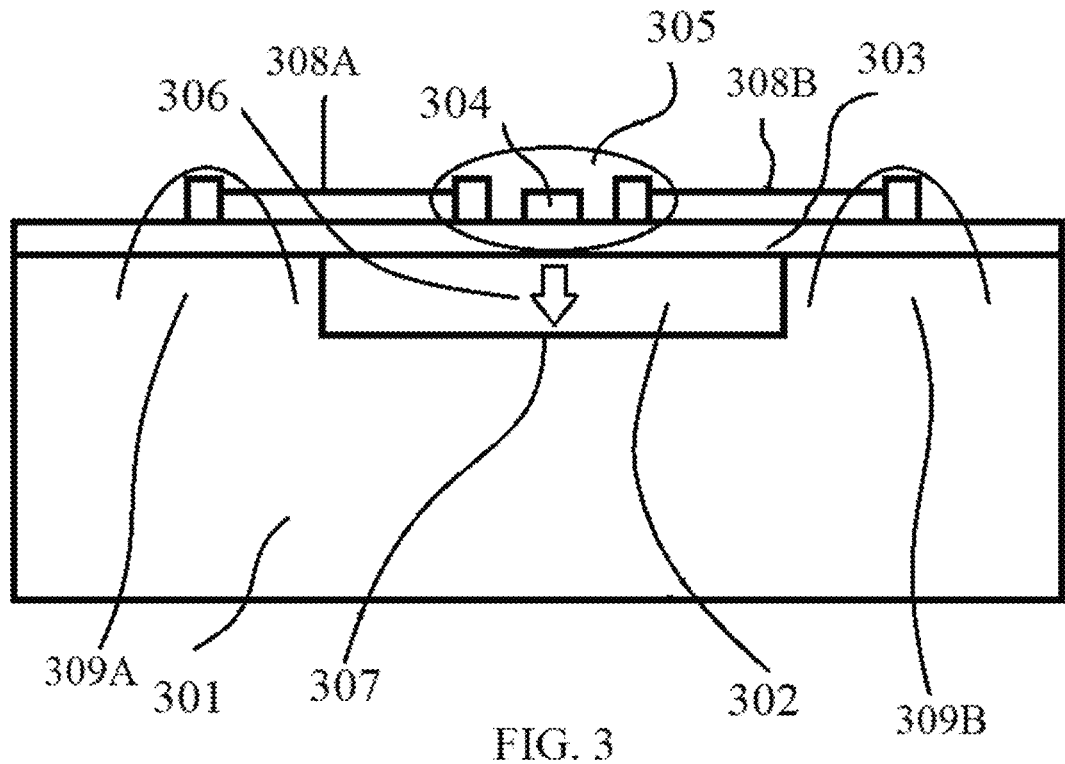
FIG. 3 is a diagram showing a MEMS thermal conductivity sensor with a one-dimensional heat transfer chamber.

Reference to FIG. 3, which is a diagram showing a MEMS thermal conductivity sensor with a one-dimensional heat transfer chamber. In FIG. 3, 301 is a silicon substrate, 302 is a chamber created in the upper region of the substrate, 303 is a thin heat insulation membrane covering the surface of the substrate including the top of the chamber, 304 is a heating resistor placed on the heat insulation membrane and at the top center region of the chamber, 305 is a heat source resulted by the energized heating resistor, 306 is a heat conduction flow from the top to the bottom of the chamber, 307 is a heat sink on the bottom of the chamber, 308*a* and 308*b* represent the two separated parts of a thermopile and 309*a* and 309*b* represent the temperature uniformed region of the substrate due to excellent thermal conductivity of single crystal silicon materials. The thermopile consists of 10 to 40 or more thermocouples and the hot junctions are placed at the heat source region and the cold junctions are placed at the top of the temperature uniformed region of the substrate so as the temperature difference measured by the thermopile really represents the temperature difference between the heat source on the top of the chamber and the heat sink on the bottom of the chamber. The vertical length of the chamber is 10 to 50 μm and the lateral length of the chamber is 400 μm to 600 μm. The area of the heat source region is 40 μm×40 μm to 80 μm×80 μm and the area of the top insulation membrane of the chamber is 400 μm×400 μm to 600 μm×600 μm. The direct distance between the cold junctions of the thermopiles and the heat sink of the chamber is in the range of 200 μm to 500 μm.

As can be seen in FIG. 3, the area occupied by the heat source region is much less than the area occupied by the heat insulation membrane on the top of the chamber and the vertical length of the chamber is much less than the lateral length of the chamber. In this case the heat transfer is restricted from the heat source to the heat sink in the vertical direction and can be calculated using a one-dimensional Fourier conduction equation:

$$Q = k \, A(T_{so} - T_{si}) / h_{so-si} \qquad (3)$$

Where Q is the rate of heat flow, k is thermal conductivity of gas in the chamber, A the lateral cross-sectional area of the chamber through which the heat flows and $T_{so}$ is the temperature of the heat source, $T_{si}$ is the temperature of the heat sink, and $h_{so-si}$ is the vertical length of the chamber.

Figure 4:
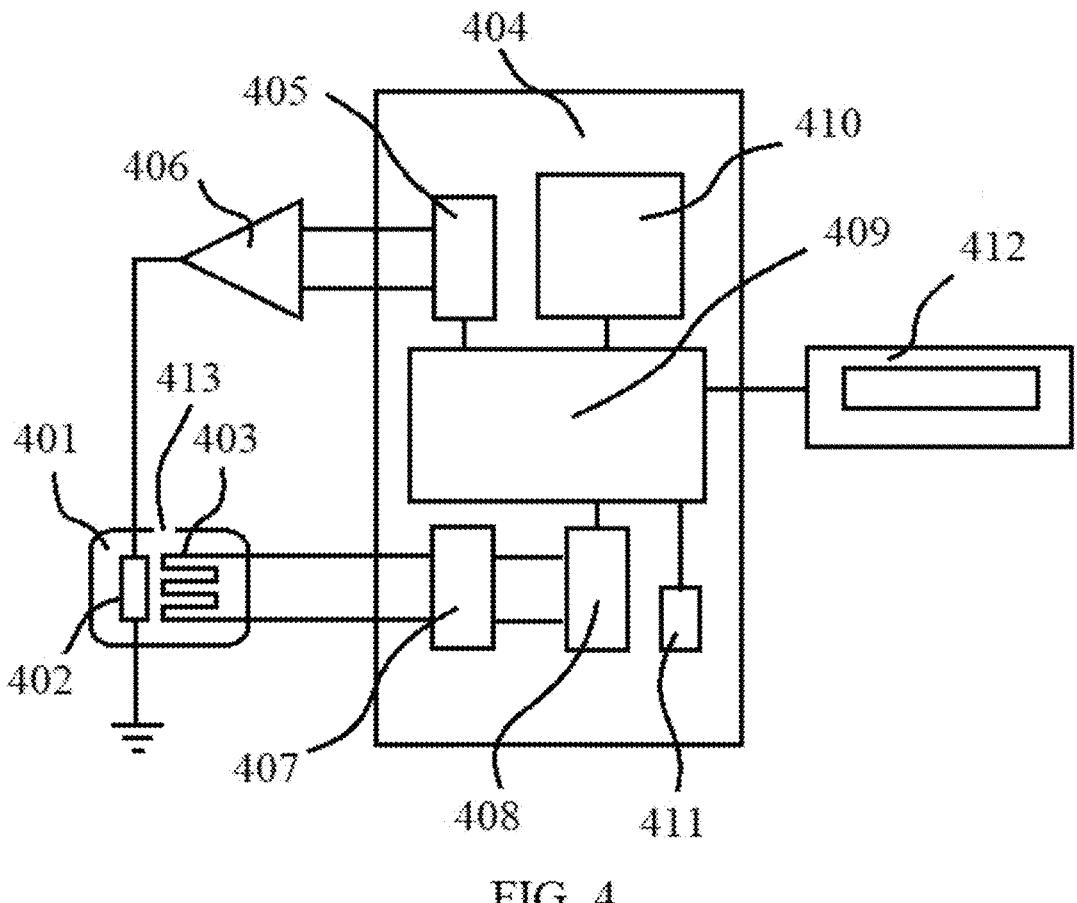
FIG. 4 is a diagram showing a single MEMS thermal conductivity sensor based system capable of simultaneously measuring air contained hydrogen and water vapor concentrations.

Reference to FIG. 4, which is a diagram showing a single MEMS thermal conductivity sensor based system capable of simultaneously measuring air contained hydrogen and water vapor concentrations. In FIG. 4, 401 is a MEMS thermal conductivity sensor, 402 is a heating resistor on the sensor chip, 403 is a thermopile on the sensor chip, 404 is a microcontroller, 405 is a pulse-width modulation (PWM) on the microcontroller chip, 406 is a voltage follower, 407 is differential amplifier on the microcontroller chip, 408 is an analog to digital converter (ADC) on the microcontroller chip, 409 is a central processing unit (CPU) on the micro-controller chip, 410 is a random-access memory (RAM) and read-only memory (ROM) on the microcontroller chip, 411 is an integrated temperature sensor on the microcontroller chip, 412 is a liquid-crystal display (LCD), 413 is an open of the MEMS thermal conductivity sensor which allows the environment gases to be measured by the sensor.

The thermopile of the MEMS thermal conductivity sensor is used to measure the temperature difference between the heat source and the heat sink of the chamber which is generated by the heat transfer from the heat source to the heat sink of the chamber. The thermopile comprises several thermocouple elements connected in series: in this way, the sensor output is increased to several times the one of a single thermocouple element. Due to the Seebeck effect, a temperature dependent voltage, proportional to the temperature difference between the hot junctions and the cold junctions, is generated.

The chamber of the MEMS thermal conductivity sensor is open to the environment so as to allow the environment gases such as an air contained hydrogen and water vapor to enter the chamber. The heat in the heat source of the sensor transfer to the heat sink through the conduction of the air contained hydrogen and water vapor in the chamber results in a change of the temperature difference between the heat source and the heat sink of the chamber which can be measured by the thermopile of the sensor.

According to the equations (2) and (3), the output signal of the sensor can be expressed as:

$$V_o = c_1 N_a + c_2 N_h + c_3 N_w + c_0 \qquad (4)$$

Where $N_a$, $N_h$, $N_w$ are the molar fractions of air, hydrogen and water vapor respectively and $c_1$, $c_2$, $c_3$ and $c_0$ are the sensitivity parameters related the molar fractions of the air, hydrogen and water vapor respectively.

Since $N_a + N_h + N_w = 1$, equation (4) can be simplified as:

$$V_o = b_h N_h + b_w N_w + b_0 \qquad (5)$$

Equation (5) can be considered as a binary linear regression equation model with two model parameters $N_h$ and $N_w$ called regression coefficients. In statistics, linear regression is a type of regression analysis that models the relationship between one or more independent variables and a dependent variable using the least squares function known as the linear regression equation. In linear regression, the data $V_0$ is modeled using a linear predictor function, and unknown model parameters $b_h$, $b_w$ and $b_0$ can be calculated using a measured data $V_0$.

To do regression analysis, a set of air samples contained hydrogen and water vapor are measured by the MEMS thermal conductivity sensor. Each air sample contains a different molar fraction $N_h$ and a different molar fraction $N_w$ and results in a different output signal $V_0$ of the sensor. Using the measured data of air samples a system such as ten binary linear equations can be created as:

$$V_{01} = b_{h1} N_{h1} + b_{w1} N_{w1} + b_{01} \qquad (6\text{-}1)$$

$$V_{010} = b_{h10} N_{h10} + b_{w10} N_{w10} + b_{010} \qquad (6\text{-}10)$$

The regression coefficients $b_1$, $b_2$, $b_0$ can be calculated through the least square evaluation by solving the equation group as:

$$\Sigma V_0 = 10 b_0 + b_h \Sigma N_h + b_w \Sigma N_w \qquad (7\text{-}1)$$

$$\Sigma N_h V_0 = b_0 \Sigma N_h + b_h \Sigma N_h^2 + b_w \Sigma N_h N_w \qquad (7\text{-}2)$$

$$\Sigma N_w V_0 = b_0 \Sigma N_w + b_h \Sigma N_h N_w + b_w \Sigma_h N_w^2 \qquad (7\text{-}3)$$

$R^2$ is the coefficient of determination, which is used as an indicator of the goodness of fit. It shows how many points fall on the regression line. The $R^2$ value is calculated from the total sum of squares, more precisely; it is the sum of the squared deviations of the original data from the mean as:

$$R^2 = 1\left[\Sigma V_0^2 - (b_0 \Sigma V_0 + b_h \Sigma N_h V_0 + b_w \Sigma N_w V_0)\right] / \left[\Sigma V_0^2 - 1/10(\Sigma V_0)^2\right] \quad (8)$$

Root mean square error percentage RMSE %, which is another goodness-of-fit measure that shows the precision of the regression analysis, the smaller is the number, the more certain is the regression equation.

$$RMSE\% = \tag{9}$$

$$\left\{\left[\left\{\Sigma V_0{}^2 - (b_0\Sigma V_0 + b_h\Sigma N_h V_0 + b_w\Sigma N_w V_0)\right\}/7\right]/V_0\right\}100$$

The system of binary linear regression equations can be computed by implementing a program written in a C programming language.

Again as shown in FIG. 1, the thermal conductivities of air, hydrogen and water vapor are all linear increase with temperature. The slopes of their curves are different and respectively have 0.0923, 0.5419, and 0.0725 in the range of −40 to 100° C. at one atmosphere. This is why the concentrations of air, hydrogen and water vapor in a gas mixture can be measured respectively using a thermal conductivity sensor through modulating the temperature of the heat source of the sensor.

The temperature modulation of a MEMS thermal conductivity sensor can be realized by change the heating voltage of the heating resistor of the sensor.

Suppose a first heating voltage produces a first modulation temperature $T_{01}$ ant at the first modulation temperature $T_{01}$ a first several air samples contained hydrogen and water vapor are measured by the MEMS thermal conductivity sensor. The first measured data are used to set up a first binary linear regression equation at the first modulation temperature as:

$$V_{01} = b_{h1}N_h + b_{w1}N_w + b_{01} \tag{10}$$

Then a second heating voltage produces a second modulation temperature $T_{02}$ and at the second modulation temperature $T_{02}$ the several air samples contained hydrogen and water vapor are measured by the MEMS thermal conductivity sensor. The second measured data are used to set up a second binary linear regression equation at the second modulation temperature as:

$$V_{02} = b_{h2}N_h + b_{w2}N_w + b_{02} \tag{11}$$

The system of binary linear regression equations (10) and (11) can be solved using a cross-multiplication method, the solution is given by $$N_h = \{b_{w1}(b_{02} - V_{02}) - b_{w2}(b_{02} - V_{02})\}/\{b_{h1}b_{w2} - b_{h2}b_{w1}\} \tag{12}$$

$$N_w = \{(b_{01} - V_{01})b_{h2} - (b_{02} - V_{02})b_{h1}\}/\{b_{h1}b_{w2} - b_{h2}b_{w1}\} \tag{13}$$

Using known hydrogen molar fraction $N_h$ and known water vapor molar fraction $N_w$ the dry air molar fraction $N_{air}$ can be calculated by:

$$N_{air} = 1 - N_h - N_w \tag{14}$$

The system of equations (12) and (13) can be solved by running a C language program.

It can be seen from equations (10) and (11), the regression coefficients $b_h$, $b_w$, $b_0$ are related to the modulation temperatures and they will be change with the modulation temperatures of the sensor. Actually the regression coefficients $b_h$, $b_w$, $b_0$ are the corresponding quantity of the thermal conductivities of hydrogen, water vapor and air itself and naturally change with the modulation temperatures.

It is reasonable to suppose that the regression coefficients $b_h$, $b_w$, $b_0$ are related to the environment temperature $T_{ent}$ by the following equations:

$$b_{h1}(T_{ent}) = \tag{15}$$

$$b_{h1}(T_{loent}) + \{[b_{h1}(T_{hient}) - b_{h1}(T_{loent})]/(T_{hient} - T_{loent})\}(T_{hient} - T_{ent})$$

$$b_{w1}(T_{ent}) = \tag{16}$$

$$b_{w1}(T_{loent}) + \{[b_{w1}(T_{hient}) - b_{w1}(T_{loent})]/(T_{hient} - T_{loent})\}(T_{hient} - T_{ent})$$

$$b_{01}(T_{ent}) = \tag{17}$$

$$b_{01}(T_{loent}) + \{[b_{01}(T_{hient}) - b_{01}(T_{loent})]/(T_{hient} - T_{loent})\}(T_{hient} - T_{ent})$$

and $$b_{h2}(T_{ent}) = \tag{18}$$

$$b_{h2}(T_{loent}) + \{[b_{h2}(T_{hient}) - b_{h2}(T_{loent})]/(T_{hient} - T_{loent})\}(T_{hient} - T_{ent})$$

$$b_{w2}(T_{ent}) = \tag{19}$$

$$b_{w2}(T_{loent}) + \{[b_{w2}(T_{hient}) - b_{w2}(T_{loent})]/(T_{hient} - T_{loent})\}(T_{hient} - T_{ent})$$

$$b_{02}(T_{ent}) = \tag{20}$$

$$b_{02}(T_{loent}) + \{[b_{02}(T_{hient}) - b_{02}(T_{loent})]/(T_{hient} - T_{loent})\}(T_{hient} - T_{ent})$$

Where $T_{loent}$ and $T_{hient}$ are the first environment temperature (lower) for creating the first binary linear regression equation and the second environment temperature (higher) for creating the second binary linear regression equation respectively and $T_{ent}$ is the environment temperature of being measured air sample contained unknown hydrogen and water vapor concentrations.

Knowing the regression coefficients $b_{h1\text{-}2}$, $b_{w1\text{-}2}$, $b_{01\text{-}2}$ at the first modulation temperature and at the second modulation temperature the MEMS thermal conductivity sensor is ready to be used for measuring any air sample contained unknown hydrogen and water vapor concentrations.

Suppose an air sample contained unknown hydrogen concentration and unknown water vapor concentration is measured by the sensor at a first modulation temperature and at a second modulation temperature respectively. The following equations can be created:

$$V_{01u} = b_{h1}N_{hu} + b_{w1}N_{wu} + b_{01} \tag{21}$$

$$V_{02u} = b_{h2}N_{hu} + b_{w2}N_{wu} + b_{02} \tag{22}$$

The unknown hydrogen molar fraction $N_{hu}$ and the unknown water vapor molar fraction $N_{hu}$ can be calculated by solving the system of equations (21) and (22) using the known regression coefficients $b_{h1\text{-}2}$, $b_{w1\text{-}2}$, $b_{01\text{-}2}$. The system of equations (15) to (20) can be used for the temperature compensation when the sensor operation temperature offsets from the original set environment temperature.

The system shown in FIG. 4, is based on a MEMS thermal conductivity sensor which is created in a silicon substrate and constructed a one dimensional gas heat conduction chamber in the substrate, a hot plate on the top of the chamber where a heating resistor is placed, a heat sink on the bottom of the chamber and a thermopile with its hot junctions in the hot plate and its cold junctions in the temperature uniformed region of the substrate where the temperature is almost the same to the heat sink.

The system further comprises a microcontroller including a nonvolatile memory (ROM), an analog-to-digital converter (ADC), a central processing unit (CPU), and a pulse-width modulation (PWM).

The system still further comprises a voltage follower (unity buffer amplifier) and a LCD (liquid crystal display).

A set of air samples contained hydrogen and water vapor is prepared and the molar fractions of hydrogen and water vapor in each sample has been measured and calibrated according to an official standard.

In operation of the MEMS thermal conductivity sensor a heating voltage is applied to the heating resistor of the sensor and a temperature difference is generated between the heat source on the top and the heat sink on the bottom of the chamber of the sensor.

The heating voltage can be produced by the PWM. The amplitude of the heating voltage can be modulated by variable-width pulses. The voltage follower provides electrical impedance transformation preventing the voltage source from being affected by the heating resistor.

The measured air sample can enter the chamber of the sensor and transfers the heat from the top to the bottom of the chamber by heat conduction and the thermopile of the sensor can produce a signal output responding the change of the measured temperature difference.

The output signal of the sensor can be amplified by the differential amplifier and converted into a digital signal by the analog-to-digital converter (ADC).

Using the measured data of the MEMS thermal conductivity sensor the microcontroller can calculate the concentrations of hydrogen and water vapor in the air samples according to a written program and the concentrations can be displayed by the liquid crystal display (LCD).

A method is summarized and extracted also from FIG. 4, which is used to operate the single MEMS thermal conductivity sensor based system for measuring the hydrogen and water vapor concentrations in an air sample and the method consists of the following steps:

Step 1, a first binary linear regression equation at a lower modulation temperature is created by measuring the air samples contained hydrogen and water vapor each having known molar fractions of hydrogen and water vapor. A first heating voltage is generated by a pulse-width-modulation duty cycle and a lower modulation temperature is produced. At the lower modulation temperature the air samples such as 10 air samples are measured by the MEMS thermal conductivity sensor successively. Using the first measured data a first binary linear regression equation is created through a binary linear regression analysis.

The created binary linear regression equation is expressed as:

$$V_{lower} = b_h(T_{lower})N_h + b_w(T_{lower})N_w + b_0(T_{lower}) \qquad (23)$$

Step 2, a second binary linear regression equation at a higher modulation temperature is created by measuring the air samples contained hydrogen and water vapor each having known molar fractions of hydrogen and water vapor. A second heating voltage is generated by a pulse-width-modulation duty cycle and a higher modulation temperature is produced. At the higher modulation temperature 10 air samples are measured by the MEMS thermal conductivity sensor successively.

Using the second measured data to create a second binary linear regression equation as:

$$V_{higher} = b_h(T_{higher})N_h + b_w(T_{higher})N_w + b_0(T_{higher}) \qquad (24)$$

Step 3, the regression coefficients $b_h(T_{lower})$, $b_w(T_{lower})$, $b_0(T_{lower})$ in equation (23) and the regression coefficients $b_h(T_{higher})$, $b_w(T_{higher})$, $b_0(T_{higher})$ in equation (24) are stored in the read-only memory (ROM) of the microcontroller.

Step 4, the single MEMS thermal conductivity sensor based system is placed in an environment air where the concentrations of the hydrogen and water vapor in the environment air are not known and need to be measured.

Step 5, the MEMS thermal conductivity sensor based system is first operated at the lower modulation temperature and a first binary linear equation is created as:

$$V_{lower}(ent) = b_h(T_{lower})N_h(ent) + b_w(T_{lower})N_w(ent) + b_0(T_{lower})(ent) \qquad (25)$$

Step 6, the MEMS thermal conductivity sensor based system is second operated at the higher modulation temperature and a second binary linear equation is created as:

$$V_{higher}(ent) = b_h(T_{higher})N_h(ent) + b_w(T_{higher})N_w(ent) + b_0(T_{higher})(ent) \qquad (26)$$

Step 7, writing a program for solving the system of binary linear equations (25) and (26) and stored in the read-only memory (ROM) of the microcontroller.

Step 8, the concentrations $N_h(ent)$ and $N_w(ent)$ of the hydrogen and water vapor in the environment air are calculated by running the program stored in the microcontroller.

The microcontroller comprises an integrated temperature sensor. The signal of the integrated temperature sensor is used by the microcontroller to carry out the temperature compensation for the measurements of the MEMS thermal conductivity sensor.

Accordingly, various modifications, adaptations, and combinations of various features of the described embodiments can be practiced without departing from the scope of the invention as set forth in the claims.

What is claimed is:

1. A single MEMS thermal conductivity sensor based system capable of simultaneously measuring an air containing hydrogen and water vapor concentrations which is operated based on: hydrogen and water vapor have different temperature coefficients of their thermal conductivities and the sensor is modulated by temperature so as to calculate their concentrations by their contributions to the total thermal conductivity of the air containing hydrogen and water vapor at different modulation temperatures of the sensor and comprises:

a MEMS thermal conductivity sensor, wherein the sensor created in a silicon substrate and has a chamber recessed in the substrate and covered with a heat insulation membrane, a temperature uniformed region in the substrate which surrounds the chamber, a heat source on the top of the chamber where a heating resistor is placed, a heat sink on the bottom of the chamber and a thermopile with its hot junctions placed in the heat source region and its cold junctions placed on the top of the temperature uniformed region where the temperature is the same as the heat sink;

a microcontroller;

a nonvolatile memory (ROM) on the microcontroller chip;

an analog-to-digital converter (ADC) on the microcontroller chip;

a central processing unit (CPU) on the microcontroller chip;

a pulse-width modulation (PWM) on the microcontroller chip;

a voltage follower (unity buffer amplifier);

a liquid crystal display (LCD);

a set of heating voltages generated by the PWM, each of them is selectively applied to the heating resistor so as to produce a modulation temperature in the heat source;

a differential amplifier amplifies the output signal of the sensor;

the analog-to-digital converter operable to convert the amplified output signal of the sensor into digital values;

a liquid crystal display (LCD) displaying the output signals of the system;

a set of air samples each containing known hydrogen concentration (in molar fraction) and known water vapor concentration (in molar fraction); and a set of air samples each containing unknown hydrogen concentration and unknown water vapor concentration which are required to be measured.

2. The system of claim 1, wherein the area of 40 μm×40 μm to 80 μm×80 μm of the heat source region is much small than the area of 400 μm×400 μm to 800 μm×800 μm of the heat insulation membrane, which facilitates one-dimensional heat transfer of gases in the chamber.

3. The system of claim 1, wherein the lateral length of 400 μm to 800 μm of the chamber is much larger than the vertical length of 10 μm to 50 μm of the chamber, which facilitates one-dimensional heat transfer of gases in the chamber.

4. The system of claim 1, wherein the chamber is open to the environment of the sensor so as to allow the environment gases such as an air containing hydrogen and water vapor to enter the chamber.

5. The system of claim 1, wherein the thermal conductivity of an air containing hydrogen and water vapor in the chamber is measured by the MEMS thermal conductivity sensor.

6. The system of claim 1, wherein the thermal conductivity of an air containing hydrogen and water vapor in the chamber is expressed as the molar averaging of the thermal conductivities of the air containing hydrogen, water vapor and air itself.

7. The system of claim 1, wherein the thermal conductivity of the air containing hydrogen and water vapor can be is expressed as a binary linear equation: $V=b_h N_h+b_w N_w+b_0$, where V is the output signal of the sensor, $N_h$ and $N_w$ are the molar fractions of the air containing hydrogen and water vapor respectively, T is the modulation temperature of the heat source of the sensor and $b_h$, $b_w$, $b_0$ are the sensitivity parameters related to the hydrogen concentration and water vapor concentration at the modulation temperature T of the sensor.

8. The system of claim 1, wherein the air containing hydrogen and water vapor have not only a special thermal conductivity but also a special temperature coefficient of the thermal conductivities so as to allow calculating the values of $N_h$ and $N_w$ by measuring the total thermal conductivity of the air containing hydrogen and water vapor at two different modulation temperatures of the sensor.

9. The system of claim 1, wherein the heating resistor is driven with a first heating voltage generated by a first pulse-width-modulation duty cycle so as to set the heat source to a first modulation temperature $T_1$ of the sensor.

10. The system of claim 1, wherein the thermal conductivity of each air sample is measured by the thermopile of the sensor at the first modulation temperature and using the first measured data a first binary regression equation: $V_1=b_{h1}N_h+b_{w1}N_w+b_{01}$ can be is created, where $V_1$ is the output signal of the sensor and $b_{h1}$, $b_{w1}$, $b_{01}$ are the calculated sensitivity parameters at first modulation temperature $T_1$ of the sensor.

11. The system of claim 1, wherein the calculated sensitivity parameters $b_{h1}$, $b_{w1}$, $b_{01}$ at the first modulation temperature $T_1$ of the sensor can be is stored in the nonvolatile memory (ROM).

12. The system of claim 1, wherein the heating resistor is driven with a second heating voltage generated by a second pulse-width-modulation duty cycle so as to set the heat source to a second modulation temperature $T_2$ of the sensor.

13. The system of claim 1, wherein the thermal conductivity of each air sample containing hydrogen and water vapor is measured by the thermopile of the sensor at the second modulation temperature of the sensor and using the second measured data a second binary regression equation: $V_2=b_{h2}N_h+b_{w2}N_w+b_{02}$ is created, where $V_2$ is the output signal of the sensor and $b_{h2}$, $b_{w2}$, $b_{02}$ are the calculated sensitivity parameters at the second modulation temperature $T_2$ of the sensor.

14. The system of claim 1, wherein the calculated sensitivity parameters $b_{h2}$, $b_{w2}$, $b_{02}$ at the second modulation temperature $T_2$ of the sensor are stored in the nonvolatile memory (ROM).

15. The system of claim 1, an application program for solving the system of the first binary linear equation and the second binary linear equation is written and stored in the nonvolatile memory (ROM).

16. The system of claim 1, wherein the first measured data of an air sample containing unknown hydrogen concentration and unknown water vapor concentration by the thermopile of the sensor at the first modulation temperature $T_1$ of the sensor is stored in the nonvolatile memory (ROM).

17. The system of claim 1, wherein the second measured data of an air sample containing unknown hydrogen concentration and unknown water vapor concentration by the thermopile of the sensor at the second modulation temperature $T_2$ of the sensor is stored in the nonvolatile memory (ROM).

18. The system of claim 1, wherein the unknown hydrogen concentration and the unknown water vapor concentration contained in the air sample are calculated using the first measured data and the second measured data by the thermopile of the sensor by running the stored application program.

19. The system of claim 1, wherein the microcontroller comprises an integrated temperature sensor for generating a temperature signal which is stored in the nonvolatile memory (ROM).

20. The system of claim 1, wherein the temperature signal stored in the nonvolatile memory (ROM) is used for the temperature compensation of the calculated hydrogen concentration and water vapor concentration contained in the air sample by running the stored application program.

21. An apparatus of single MEMS thermal conductivity sensor based system simultaneously measuring an air containing hydrogen and water vapor concentrations is operated based on hydrogen and water vapor having different temperature coefficients of their thermal conductivities and the sensor able to be modulated by temperature so as to calculate their concentrations by their contributions to the total thermal conductivity of the air containing hydrogen and water vapor at different modulation temperatures of the sensor and the apparatus involves:

a MEMS thermal conductivity sensor, wherein the sensor created in a silicon substrate and has a chamber recessed in the substrate and covered with a heat insulation membrane, a temperature uniformed region in the substrate which surrounds the chamber, a heat source on the top of the chamber where a heating resistor is placed, a heat sink on the bottom of the chamber and a thermopile with its hot junctions placed in the heat source region and its cold junctions placed on the top of the temperature uniformed region where the temperature is the same as the heat sink;

a microcontroller;

a nonvolatile memory (ROM) on the microcontroller chip;

an analog-to-digital converter (ADC) on the microcontroller chip;

a central processing unit (CPU) on the microcontroller chip;

a pulse-width modulation (PWM) on the microcontroller chip;

a voltage follower (unity buffer amplifier);

a liquid crystal display (LCD);

a set of heating voltages generated by the PWM, each of them is selectively applied to the heating resistor so as to produce a modulation temperature in the heat source;

a differential amplifier amplifies the output of the sensor;

the analog-to-digital converter operable to convert the amplified output signal of the sensor into digital values;

a liquid crystal display (LCD) displaying the output signals of the system;

a set of air samples each containing either known or unknown hydrogen and water concentrations (in molar fraction).

22. The apparatus of claim 21, wherein the area of 40 μm×40 μm to 80 μm×80 μm of the heat source region is much small than the area of 400 μm×400 μm to 800 μm×800 μm of the heat insulation membrane, which facilitates one-dimensional heat transfer of gases in the chamber.

23. The apparatus of claim 21, wherein the lateral length of 400 μm to 800 μm of the chamber is much larger than the vertical length of 10 μm to 50 μm of the chamber, which facilitates one-dimensional heat transfer of gases in the chamber.

24. The apparatus of claim 21, wherein the chamber is open to the environment of the sensor so as to allow the environment gases such as an air containing hydrogen and water vapor to enter the chamber.

25. The apparatus of claim 21, wherein the thermal conductivity of an air containing hydrogen and water vapor in the chamber is measured by the MEMS thermal conductivity sensor.

26. The apparatus of claim 21, wherein the thermal conductivity of the air containing hydrogen and water vapor in the chamber is expressed as the molar averaging of the thermal conductivities of the air containing hydrogen, water vapor and air itself.

27. The apparatus of claim 21, wherein the thermal conductivity of the air containing hydrogen and water vapor is expressed as a binary linear equation: $V=b_h N_h+b_w N_w+b_0$, where V is the output signal of the sensor, $N_h$ and $N_w$ are the molar fractions of the air containing hydrogen and water vapor respectively, Tis the modulation temperature of the heat source of the sensor and $b_h$, $b_w$, $b_0$ are the sensitivity parameters related to the hydrogen concentration and water vapor concentration at the modulation temperature T of the sensor.

28. The apparatus of claim 21, wherein the air containing hydrogen and water vapor have not only special thermal conductivities but also special temperature coefficients of their thermal conductivities so that the apparatus calculates the values of $N_h$ and $N_w$ by measuring the total thermal conductivity of the air containing hydrogen and water vapor at two different modulation temperatures of the sensor.

29. The apparatus of claim 21, wherein the heating resistor is driven with a first heating voltage generated by a first pulse-width-modulation duty cycle so as to set the heat source to a first modulation temperature $T_1$ of the sensor.

30. The apparatus of claim 21, wherein the thermal conductivity of each air sample is measured by the thermopile of the sensor at the first modulation temperature and using the first measured data a first binary regression equation: $V_1=b_{h1}N_h+b_{w1}N_w+b_{01}$ is created, where $V_1$ is the output signal of the sensor and $b_{h1}$, $b_{w1}$, $b_{01}$ are the calculated sensitivity parameters at the first modulation temperature $T_1$ of the sensor.

31. The apparatus of claim 21, wherein the calculated sensitivity parameters $b_{h1}$, $b_{w1}$, $b_{01}$ at the first modulation temperature $T_1$ of the sensor are stored in the nonvolatile memory (ROM).

32. The apparatus of claim 21, wherein the heating resistor is driven with a second heating voltage generated by a second pulse-width-modulation duty cycle so as to set the heat source to a second modulation temperature $T_2$ of the sensor.

33. The apparatus of claim 21, wherein the thermal conductivity of each air sample containing hydrogen and water vapor is measured by the thermopile of the sensor at the second modulation temperature of the sensor and using the second measured data a second binary regression equation: $V_2=b_{h2}N_h+b_{w2}N_w+b_{02}$ is created, where $V_2$ is the output signal of the sensor and $b_{h2}$, $b_{w2}$, $b_{02}$ are the calculated sensitivity parameters at the second modulation temperature $T_2$ of the sensor.

34. The apparatus of claim 21, wherein the calculated sensitivity parameters $b_{h2}$, $b_{w2}$, $b_{02}$ at the second modulation temperature $T_2$ of the sensor are stored in the nonvolatile memory (ROM).

35. The apparatus of claim 21, an application program for solving the system of the first binary linear equation and the second binary linear equation is written and stored in the nonvolatile memory (ROM).

36. The apparatus of claim 21, wherein the first measured data of an air sample containing unknown hydrogen concentration and unknown water vapor concentration by the thermopile of the sensor at the first modulation temperature $T_1$ of the sensor is stored in the nonvolatile memory (ROM).

37. The apparatus of claim 21, wherein the second measured data of an air sample containing unknown hydrogen concentration and unknown water vapor concentration by the thermopile of the sensor at the second modulation temperature $T_2$ of the sensor is stored in the nonvolatile memory (ROM).

38. The apparatus of claim 21, wherein the unknown hydrogen concentration and the unknown water vapor concentration contained in the air sample are calculated using the first measured data and the second measured data by the thermopile of the sensor by running the stored application program.

39. The apparatus of claim 21, wherein the microcontroller comprises an integrated temperature sensor for generating a temperature signal which is stored in the nonvolatile memory (ROM).

40. The apparatus of claim 21, wherein the temperature signal stored in the nonvolatile memory (ROM) is used for the temperature compensation of the calculated hydrogen concentration and water vapor concentration contained in the air sample by running the stored application program.

* * * * *